United States Patent [19]

Chao

[11] Patent Number: 4,837,356
[45] Date of Patent: Jun. 6, 1989

[54] PROCESS FOR THE PREPARATION OF ALKYL 4-KETOALKANOATES

[75] Inventor: Kuo-Hua Chao, Houston, Tex.

[73] Assignee: Shell Oil Company, Houston, Tex.

[21] Appl. No.: 111,952

[22] Filed: Oct. 23, 1987

[51] Int. Cl.$^4$ ............................................. C07C 69/66
[52] U.S. Cl. ...................................... 560/174; 560/175
[58] Field of Search ................................ 560/175, 174

[56] References Cited

U.S. PATENT DOCUMENTS 2,542,767  2/1951  Gresham et al. .................. 560/175
3,816,488  6/1974  Craddock et al. .................. 560/175

Primary Examiner—Werren B. Lone

[57] ABSTRACT

Methyl-4-ketohexanoate is prepared by reacting methyl acrylate, ethylene, carbon monoxide and a secondary alcohol, e.g. a secondary alcohol having 3 to 20 carbon atoms, in the presence of a catalyst comprising a complex combination of rhodium, carbon monoxide and triorganophosphorus.

6 Claims, No Drawings

PROCESS FOR THE PREPARATION OF ALKYL 4-KETOALKANOATES

FIELD OF THE INVENTION

This invention relates to the preparation of alkyl 4-ketoalkanoates from alkyl 2-alkenoates, carbon monoxide, ethylene and a secondary alcohol. It particularly relates to the preparation of methyl 4-ketohexanoate from methyl acrylate.

BACKGROUND OF THE INVENTION

Alkyl 4-ketoalkanoates have a variety of commercially important uses; for example, as intermediates for organic synthesis. Ketoalkanoic acids are used industrially in the manufacture of rubbers, plastics and medicinals. Methyl 4-ketohexanoate can, for example, be cyclized to provide 2-methylcyclopentane-1,3-dione. This latter compound and its 2-polycarbonalkyl homologs, such as 2-ethylcyclopentane-1,3-dione, prepared from methyl 4-ketoheptanoate, are of substantial importance in the preparation of therapeutically-active-totally-synthetic steroids such as estrone, estradiol, 19-nortestosterone and the like. Alkyl 4-ketoalkanoates have been made by the reaction of a secondary nitroparaffin with aqueous sodium hydroxide yielding the sodium salt of the corresponding aci-nitro compound, which is treated with strong mineral acids to give ketones (the so-called "Nef" reaction). The acids are subsequently esterified. U.S. Pat. No. 3,492,337, issued Jan. 27, 1970 uses a similar process, but uses a strong mineral acid in an alcohol solution to directly produce the ketoalkanoate. The process of the instant invention avoids the use of nitro compounds and uses readily available $\alpha$-$\beta$ unsaturated acid esters, such as methyl acrylate as a feedstock.

SUMMARY OF THE INVENTION

This invention relates to a process for the preparation of alkyl 4-ketoalkanoates wherein the alkyl is preferably selected from $C_1$-$C_3$ alkyl, which process comprises reacting an alkyl acrylate with ethylene, carbon monoxide and a secondary alcohol in the presence of a catalyst comprising rhodium in complex combination with carbon monoxide and a tri-organophosphorous compound.

DETAIL DESCRIPTION OF THE INVENTION

The starting feedstock of the instant process is an alkyl acrylate. The term "acrylate" as used herein refers to an alkyl ester of acrylic acid. It is understood that the acrylic acid may be an unsubstituted or a lower alkyl substituted acrylic acid. Examples of the lower alkyl substituted acrylic acids are methacrylic acid, crotonic acid and the like. The alkyl portion of the acrylate ester is lower alkyl i.e., from 1 to about 3 carbon atoms. Depending on the particular acrylate utilized as the starting material, the end product alkyl 4-ketoalkanoate may or may not be substituted with lower alkyls. For example, an acrylate feedstock will produce a hexanoate; a methacrylate feedstock will produce a 2-methyl-4-ketohexanoate; and a crotonate will produce a 4-ketoheptanoate (or 6-methyl-4-ketohexanoate).

Carbon monoxide and ethylene are also co-reactants in the instant process. These are suitably charged as gases to the reactor, preferably under pressure. Typically pressures of the ethylene and/or carbon monoxide will range from about 1 atmosphere to about 10 atmospheres, although higher pressures can be utilized, although at greater expense. Preferably the carbon monoxide and ethylene will be applied to the reaction in a 1 to 1 molar ratio.

A fourth reactant in the instant process is a secondary alcohol. This alcohol serves two purposes. First, it serves as a solvent for the reaction media and second, it provides a labile hydrogen needed by the reaction. During the reaction the secondary alcohol will be converted to a ketone which can be separated from the reaction products and sold as a valuable by-product or reduced back to the alcohol and recycled. Suitable alcohols are those alcohols which are liquids at the operating conditions. Preferred alcohols are the lower secondary alcohols. Examples are of suitable alcohols are isopropanol, 2-butanol, 2-pentanol, 3-pentanol, 2-hexanol, 3-hexanol, and the like. At least two moles of secondary alcohol will be required for each mole of acrylate feedstock. Preferably, the alcohol is present in excess, that is greater than 2 moles of alcohol per mole of acrylate feedstock. Preferably, the molar ratio of alcohol to acrylate will range from about 3 to about 10.

The catalyst useful in the process of the instant invention comprise rhodium in complex combination with carbon monoxide and a triorganophosphous compound. Those rhodium-carbon monoxide-phosphous ligand catalysts which are used in hydroformylation processes are readily suitable for the instant process. Illustrative examples of those catalysts as used in hydroformylation processes can be found in U.S. Pat. No. 3,499,932, issued Mar. 10, 1970; U.S. Pat. No. 3,527,809, issued Sept. 8, 1970 and British Patent specification 1,338,237, published Nov. 21, 1973. These catalytic complexes of rhodium are also readily available from commercial sources. For example, the hydridocarbonyltris(triphenylphosphine)rhodium (I) can be purchased from Aldrich Chemical Company.

The catalysts which are contemplated comprise rhodium in complex combination with carbon monoxide and a ligand containing a trivalent atom of phosphorus, said trivalent atom possessing one available pair of electrons. The ligand is a tertiary organo phosphorous compound wherein each oregano moiety is composed of (1) carbon and hydrogen atoms, or (2) carbon, hydrogen, and aliphatic etheric oxygen atoms, each of the organo moieties being monovalently bonded to the trivalent phosphorus through a carbon atom or an aliphatic etheric oxygen atom thereof. The organo moieties can also contain other substituents such as cyano and halo, e.g., chloro. The term "aliphatic etheric oxygen atom," as used herein, is meant to convey the —O— group which does not form part of a heterocyclic ring such as, for example, dioxane. Consequently, the —O— groups present in, for instance, the trialkylphosphites or the triarylphosphites are considered, for purposes of our definition, to be "aliphatic etheric oxygen atoms." Strictly speaking, through, the oxygen atom in the trialkylphosphites and the triarylphosphites stem from the corresponding acid, i.e, phosphorous acid. As such various authorities consider the phosphite compounds to be esters. The term "complex" as used herein including the claims, means a coordination compound formed by the union of one or more electronically rich molecules or atoms capable of independent existence with one or more electronically poor molecules or atoms, each of which is also capable of independent existence.

The stabilizing phosphorus-containing ligands are selected from the group consisting of phosphines, phosphinites, phosphonites, and phosphites.

The preferred phosphine ligands which are useful in stabilizing the catalyst used in the process of this invention are triorgano phosphines of the general formula $R_3 P$ wherein R independently is an organo group having from 1 to 20 carbon atoms, preferably from 1 to 10 carbon atoms and having only aromatic unsaturation. R is therefore saturated aliphatic, including cycloaliphatic, or is aromatic in character, preferably mononuclear aromatic, and is hydrocarbyl, that is, contains only atoms of carbon and hydrogen, or is substituted hydrocarbyl containing, besides atoms of carbon and hydrogen, other atoms such as oxygen, sulfur, nitrogen and halogen, particularly halogen of atomic number from 9 to 35, which atoms are present in functional groups such as alkoxy, carbalkoxy, acyl, trihalomethyl, halo, cyano, dialkylamino, sulfonylalkyl, alkanoyloxy and like groups having no active hydrogen atoms.

Illustrative of suitable saturated aliphatic R groups are hydrocarbyl R groups such as methyl, ethyl, propyl, isopropyl, butyl, isooctyl, decyl, lauryl, stearyl, cyclohexyl, cyclopentyl, 3,4-dimethylcyclopentyl, cyclooctyl, benzyl and p-phenylethyl, as well as substituted groups such as 4-bromohexyl, methoxymethyl, 3-(diethylamino)propyl, 4-carbethoxybutyl and 2-acetoxyethyl. Aromatic R groups include hydrocarbyl aromatic groups such as phenyl, tolyl, xylyl, p-ethylphenyl, p-tertbutylphenyl, m-octylphenyl, 2,4-diethylphenyl, p-phenylphenyl, m-benzylphenyl and 2,4,6-trimethylphenyl, and substituted hydrocarbyl aromatic R groups including p-methoxyphenyl, m-chlorophenyl, m-trifluoromethylphenyl, p-propoxyphenyl, p-carbethoxyphenyl, 2,4-dichlorophenyl, 2-ethyl-5 bromophenyl, p-dimethylaminophenyl, m-diethylaminophenyl, 3,5-dibutoxyphenyl, p-acetoxyphenyl, 2-hexyl-3-methylsulfonylphenyl, 3,5-bis(trichloromethyl)phenyl and 3-dibutylaminophenyl. Suitable aromatic R groups will preferably have 6 to about 20, more preferably 6 to about 10 carbon atoms.

In the $R_3 P$ ligand as defined above, the R moieties are the same or are different, although ligands wherein all R groups are the same are generally preferred for economic reasons.

It is also suitable for an organic radical to satisfy more than one of the valences of the phosphorus atom, thereby forming a heterocyclic compound with a trivalent phosphorus atom. For example, an alkylene radical may satisfy two phosphorus valences with its two open valences and thereby form a cyclic compound. Another example would be the alkylene dioxy radical to form a cyclic compound where oxygen atoms link an alkylene radical to the phosphorus atom. In these two examples, the third phosphorus valance may be satisfied by any other organic radical.

Another type of structure involving trivalent phosphorus having an available pair of electrons are those containing a plurality of such phosphorus atoms linked by organic radicals. This type of a compound is called a bidentate ligand when two such phosphorus atoms are present, a tridentate liquid when three such phosphorus atoms are present, and so forth.

The instant process is effected in the presence of the catalytically significant quantity of the rhodium complex catalyst. The reaction will proceed when employing as little as about $1 \times 10^{-6}$ mole, and even lesser amounts of rhodium (from the complex catalyst) per mole of acrylate feed. However, such catalyst concentrations, though operable are not particularly desirable since the reaction rate will be relatively slow and thus not commercially attractive. The upper catalyst concentration limit can be as high as about $1 \times 10^{-1}$ mole, and higher, of rhodium per mole of acrylate feed. However, the upper limit appears to be dictated and controlled more by economics in view of the high cost of rhodium metal and rhodium compounds. No particular advantages at such relatively high concentrations are manifest. A catalyst concentration of from about $1 \times 10^{-5}$ mole to about $5 \times 10^{-2}$ mole of rhodium metal per mole of acrylate feed is desirable. A concentration of from about $1 \times 10^{-4}$ to about $1 \times 10^{-2}$ mole of rhodium per mole of acrylate feed is preferred. It is apparent, however, that the concentration of the complex catalyst can vary over a wide range.

The operating conditions of the instance process will depend on the particular reactants utilized. In general, the operating temperature will range from about 100° C. to about 300° C. and the operating pressure will range from about atmospheric to about 10 atmospheres.

The process of the instant invention may be accomplished in either a batch or continuous type of operation. For example, when a batch operation is to be employed, a quantity of the catalyst, methyl acrylate substrate, and secondary alcohol will be placed in a pressure-resistant apparatus, such as an autoclave of the stirring, mixing or rotating type. Following the addition of the catalyst and the starting materials, the apparatus is sealed, flushed with an inert gas such as nitrogen, and pressurized to the desired operating pressure with carbon monoxide and ethylene. Upon reaching the desired operating pressure, the apparatus is then heated to a predetermined operating temperature and maintained thereat for the desired residence time which may range from about 0.5 up to about 20 hrs. or more in duration. Upon completion of the desired residence time, heating is discontinued and after the apparatus and contents thereof have returned to room temperature, the excess pressure is discharged, the apparatus is opened, and the reaction mixture is recovered therefrom. Product methyl 4-ketohexanoate is separated from the reaction mixture by conventional means, such as by fractional distillation, fractional crystallization, etc.

It is contemplated within the scope of this invention that the instant process may be accomplished in a continuous manner of operation. When such a type of operation is employed the reactants i.e., the alkyl acrylate, sec-alcohol, ethylene and carbon monoxide are continuously charged to an apparatus which is maintained at the proper operating conditions of temperature and pressure. In addition, the complex which is to be employed is also continuously charged to the reaction apparatus either through separate lines or, if so desired, the components of the reaction mixture may be admixed prior to entry into the reaction apparatus and the resulting mixture charged thereto to a single stream. After passage through the apparatus for a predetermined period of time, the reactor effluent is continuously withdrawn and subjected to conventional means of separation whereby the product mix is separated from the catalyst and any other unreacted starting material that is to be recycled to the reaction apparatus to form a portion of the feedstock, while the product mix is further subjected to distillation to recover the various components of the mix.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The process of the instant invention is further described by the following example which is provided for illustration and is not to be construed as limiting the invention.

EXAMPLE 1

To a 100 cc stainless steel screw top autoclave was added 168 ml (0.183 mmole) of hydridocarbonyltris(triphenylphosphine)rhodium (I), 9 ml (100 mmole) of methyl acrylate, 31 ml (405 mmole) of isopropanol. The autoclave was sealed under a nitrogen atmosphere and flushed with carbon monoxide, following which the autoclave was pressured with 400 psi ethylene and 400 psi carbon monoxide. Thereafter, the autoclave was heated to a temperature of about 180° C. and maintained there for a period of about 4 hrs. At the end of this period, heating was discontinued and the autoclave was allowed to return to room temperature. The excess pressure was discharged, the autoclave was opened, and the reaction product was recovered. The product was analyzed by means of gas liquid chromatography and mass spectropraphy. This analysis determine that there had beedn a 87% wt. conversion of the methyl acrylate with a selectivity of 61% to methyl 4-ketohexanoate acid, and with a selectivity of 30% to methyl proprionate. The catalyst turnover for this reaction was 475, that is 475 parts of methyl acrylate converted per part of rhodium catalyst present.

I claim:

1. A process for the preparation of alkyl 4-ketohexanoate which comprises reacting alkyl acrylate, ethylene, carbon monoxide and a secondary alcohol in the presence of a catalyst comprising rhodium in complex combination with carbon monoxide and a triorgano phosphorus compound selected from the group consisting of phosphines, phosphinites, phosphonites and phosphites at a temperature ranging from about 100° C. to about 300° C. and at a pressure ranging from about atmospheric to about 10 atmospheres.

2. The process of claim 1 wherein the alkyl group contains 1 to about 3 carbon atoms and the secondary alcohol contains from 3 to about 20 carbon atoms.

3. The process of claims 1 or 2 wherein the triorgano phosphorus compound has the general formula $R_3P$ wherein R is alkyl, aralkyl or aryl having from 1 to about 20 carbon atoms.

4. The process of claim 3 wherein R is alkyl having from 1 to about 10 carbon atoms.

5. The process of claim 3 wherein R is aryl having from 6 to about 10 carbon atoms.

6. The process of claim 5 wherein R is phenyl.

* * * * *